United States Patent
Gupta et al.

(10) Patent No.: US 9,279,146 B2
(45) Date of Patent: Mar. 8, 2016

(54) COMPOUNDS AND METHODS FOR THE ENRICHMENT OF MUTATED NUCLEIC ACID FROM A MIXTURE

(71) Applicant: Roche Molecular Systems, Inc., Pleasanton, CA (US)

(72) Inventors: Amar Gupta, Danville, CA (US); Nancy Schoenbrunner, Moraga, CA (US)

(73) Assignee: ROCHE MOLECULAR SYSTEMS, INC., Pleasanton, CA (US)

(*) Notice: Subject to any disclaimer, the term of this patent is extended or adjusted under 35 U.S.C. 154(b) by 81 days.

(21) Appl. No.: 14/098,789

(22) Filed: Dec. 6, 2013

(65) Prior Publication Data

US 2014/0308664 A1    Oct. 16, 2014

Related U.S. Application Data

(60) Provisional application No. 61/740,895, filed on Dec. 21, 2012.

(51) Int. Cl.
*C12Q 1/68*      (2006.01)
*C07F 15/00*    (2006.01)

(52) U.S. Cl.
CPC .......... *C12Q 1/6806* (2013.01); *C07F 15/0073* (2013.01); *C12Q 1/6827* (2013.01)

(58) Field of Classification Search
None
See application file for complete search history.

(56) References Cited

U.S. PATENT DOCUMENTS

| | | | |
|---|---|---|---|
| 6,031,098 A | 2/2000 | Barton et al. | |
| 6,120,992 A | 9/2000 | Wagner, Jr. | |
| 6,306,601 B1 | 10/2001 | Barton et al. | |
| 6,444,661 B1 | 9/2002 | Barton et al. | |
| 6,630,301 B1 | 10/2003 | Gocke et al. | |
| 6,777,405 B2 | 8/2004 | Barton et al. | |
| 7,094,543 B2 | 8/2006 | Li-Sucholeiki et al. | |
| 7,345,172 B2 | 3/2008 | Barton et al. | |
| 7,935,484 B2 | 5/2011 | Gocke et al. | |
| 8,053,188 B2 | 11/2011 | Gullberg et al. | |
| 8,076,082 B2 | 12/2011 | Guo | |
| 2011/0003282 A1 | 1/2011 | Wain-Hobson et al. | |
| 2011/0217714 A1 | 9/2011 | Makrigiorgos | |
| 2012/0164641 A1 | 6/2012 | Bauer et al. | |

FOREIGN PATENT DOCUMENTS

| WO | 0105800 A2 | 1/2001 |
|---|---|---|
| WO | 0105800 A3 | 1/2001 |
| WO | 2007084380 A2 | 7/2007 |
| WO | 2007084380 A3 | 7/2007 |
| WO | 2013/077282 | 2/2014 |

OTHER PUBLICATIONS

Asano, H. et al., Clin. Cancer Res. 2006, 12(1): 43-48; Detection of EGFR gene mutation in lung cancer by mutant-enriched polymerase chain reaction assay.
Benesova L. et al., Analytical Biochemistry 2013, 433(2):227-34; Mutation-based detection and monitoring of cell-free tumor DNA in peripheral blood of cancer patients.
Boon, E.M et al., Methods in Enzymology 2002, 353:506-522; Detection of DNA base mismatches using DNA intercalators.
Jackson, B.A. & Barton, J.K., Biochemistry 2000, 39: 6176-6182; Recognition of base mismatches in DNA by 5,6-chrysenequinone diimine complexes of rhodium(III): a proposed mechanism for preferential binding in destabilized regions of the double helix.
Li, J. et al., Nature Medicine 2008, 14(5): 579-584; Replacing PCR with COLD-PCR enriches variant DNA sequences and redefines the sensitivity of genetic testing.
Milbury, C.A. et al., Clinical Chemistry 2009, 55(4): 632-640; PCR-based methods for the enrichment of minority alleles and mutations.
Nollau, P. et al., Int. J. Cancer 1996, 66: 332-336; Detection of K-ras mutations in stools of patients with colorectal cancer by mutant-enriched PCR.
Zeglis, B.M. & Barton, J.K.. Nature Protocols 2007, 2(2): 357-371.

*Primary Examiner* — James Martinell
(74) *Attorney, Agent, or Firm* — David J Chang

(57) ABSTRACT

The detection of the presence of rare somatic mutations from a biological sample is often challenging due to the simultaneous presence of a vast excess of wild-type DNA. The present invention describes novel compounds and methods that would allow the enrichment of mutant DNA by depleting amplifiable wild-type DNA.

12 Claims, 5 Drawing Sheets

COMPOUNDS AND METHODS FOR THE ENRICHMENT OF MUTATED NUCLEIC ACID FROM A MIXTURE

CROSS REFERENCE TO RELATED INVENTION

This application claims the benefit of priority of U.S. Provisional Patent Application Ser. No. 61/740,895, filed Dec. 21, 2012, which is incorporated herein by reference in its entirety.

FIELD OF THE INVENTION

The invention pertains to the fields of nucleic acid chemistry and nucleic acid amplification. In particular, the invention pertains to the enrichment of low abundance mutant target nucleic acids using compounds and methods that can detect base pair mismatches in nucleic acids.

BACKGROUND OF THE INVENTION

Most human inherited diseases and cancers are known to be caused by mutations in nuclear genes. In general, a mutation is considered to be particular polymorphic variants at a genetic locus. The mutation can be a single nucleotide difference, often referred to as a point mutation. At the cellular and tissue level, polymorphisms at a specific genetic locus may give rise to significantly altered cellular behavior. However, because even relatively small cell or tissue samples can contain millions or billions of DNA molecules containing the particular genetic locus, a representation of the range and frequencies of polymorphic variants at a genetic locus, requires detecting alleles that are potentially present at a very low frequency. In most cases, the detection of the presence of rare mutations from a biological sample presents tremendous challenges due to the simultaneous presence of a vast excess of wild-type DNA.

Thus there exists a need in the art for a method to selectively and accurately enrich low-copy mutant DNA such that their presence can be detectable following the performance of amplification reactions such as PCR.

SUMMARY OF THE INVENTION

The present invention is directed to methods and compositions for enriching low abundance alleles (e.g. mutant DNA) in a sample that allows subsequent detection of such alleles. In a first aspect, the invention relates to a method of enriching a variant of a target nucleic acid sequence in a mixture of nucleic acids from a sample, the target nucleic acid existing in the form of two variant sequences, wherein said variants differ at a single nucleotide position, the method comprising, providing the sample that includes the target nucleic acid sequence wherein the variant to be enriched is present in the sample in low abundance amongst a large excess of the other variant; providing an oligonucleotide that is complementary to one strand of the target nucleic acid sequence, wherein the oligonucleotide has a mismatch at the single nucleotide position with the variant to be enriched and is perfectly matched at the single nucleotide position with the other variant; providing conditions suitable for hybridization of the oligonucleotide to the target nucleic acid to generate duplex polynucleotides consisting of the oligonucleotide and one strand of either variant of the target nucleic acid sequence; contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch; subjecting the reaction mixture to an affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence.

In a second aspect, the invention relates to a method for detecting a mutant allele of a target nucleic acid sequence in a mixture of nucleic acids from a sample wherein the mutant allele differs from a wild-type allele at a single nucleotide position and is present in the sample in low abundance amongst a large excess of the wild-type allele, the method comprising, enriching the mutant allele in the sample wherein the enrichment is performed by providing an oligonucleotide that is complementary to one strand of the target nucleic acid sequence, wherein the oligonucleotide has a mismatch at the single nucleotide position with the mutant allele and is perfectly matched at the single nucleotide position with the wild-type allele; providing conditions suitable for hybridization of the oligonucleotide to the target nucleic acid to generate duplex polynucleotides consisting of the oligonucleotide and one strand of either the mutant allele or the wild-type allele; contacting the duplex polynucleotides with a mismatch intercalating compound that is attached with an affinity label to generate a reaction mixture, wherein the mismatch intercalating compound is capable of binding to the duplex polynucleotides that contain a mismatch and is not capable of binding to the duplex polynucleotides that do not contain a mismatch; subjecting the reaction mixture to a affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched mutant allele; amplifying the enriched mutant allele; and detecting the product of the enriched amplified mutant allele or the signal generated from the enriched amplified mutant allele.

In a third aspect, the invention relates to a method of enriching a variant of a target nucleic acid sequence in a mixture of nucleic acids from a sample, the target nucleic acid existing in the form of two variant sequences, wherein said variants differ at a single nucleotide position, the method comprising: providing the sample that includes the target nucleic acid sequence wherein the variant to be enriched is present in the sample in low abundance amongst a large excess of the other variant; heating the sample such that the mixture of nucleic acid is denatured; providing conditions suitable for the reannealing of the target nucleic acid, wherein duplex polynucleotides can be formed between one strand of one variant sequence and one strand of the other variant sequence to generate a mismatch at the single nucleotide position where the variants differ; contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch; subjecting the reaction mixture to an affinity matrix that recognizes and binds to the affinity label on the mismatch intercalating compound;

washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence.

In a fourth aspect, the invention relates to a method for detecting a mutant allele of a target nucleic acid sequence in a mixture of nucleic acids from a sample wherein the mutant allele differs from a wild-type allele at a single nucleotide position and is present in the sample in low abundance amongst a large excess of the wild-type allele, the method comprising: enriching the mutant allele in the sample wherein the enrichment is performed by: heating the sample such that the mixture of nucleic acid is denatured; providing conditions suitable for the reannealing of the target nucleic acid, wherein duplex polynucleotides can be formed between one strand of the mutant allele and one strand of the wild-type allele to generate a mismatch at the single nucleotide position where the alleles differ; contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch; subjecting the reaction mixture to an affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence; amplifying the enriched mutant allele; and detecting the product of the enriched amplified mutant allele or the signal generated from the enriched amplified mutant allele.

In a fifth aspect, the invention relates to a compound for enriching rare allelic DNA wherein said compound is the compound of FIG. 2.

DETAILED DESCRIPTION OF THE INVENTION

Definitions

Figure 1:
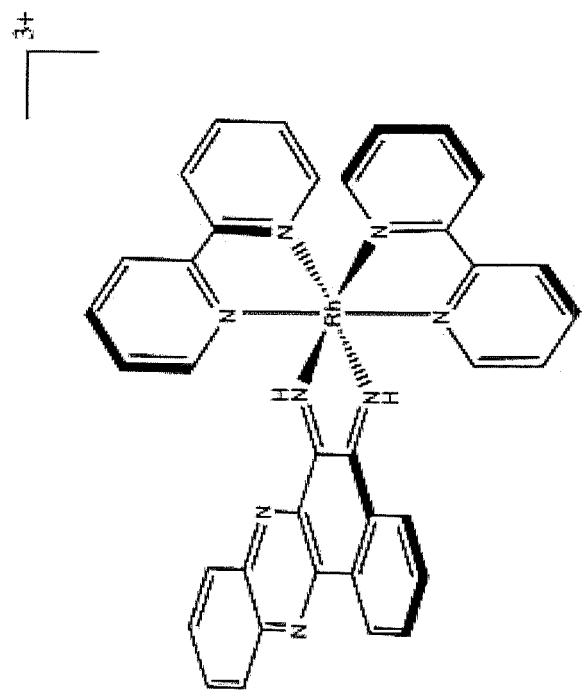
FIG. 1 shows the structures of the rhodium-based intercalators, $Rh(bpy)_2(chrysi)^{3+}$ (left) and $Rh(bpy)_2(phzi)^{3+}$ (right).
Figure 1:
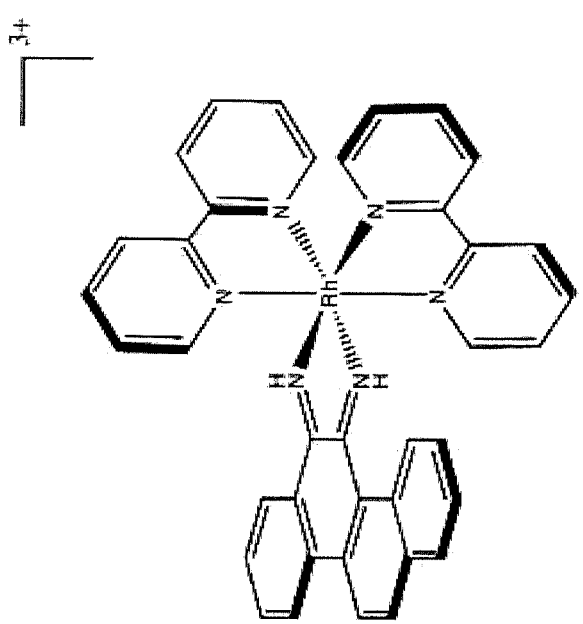

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphosphoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

The terms "polynucleotide" and "oligonucleotide" are used interchangeably. "Oligonucleotide" is a term sometimes used to describe a shorter polynucleotide. An oligonucleotide may be comprised of at least 6 nucleotides, for example at least about 10-12 nucleotides, or at least about 15-30 nucleotides corresponding to a region of the designated nucleotide sequence.

The term "enriching a variant of a target nucleic acid sequence" refers to increasing the amount of the desired variant of the target nucleic acid sequence and increasing the ratio of the desired variant relative to the undesired variant in a sample. Generally, the desired variant to be enriched is less prevalent in a nucleic acid sample than the undesired variant, and makes up less than 50% of the total amount of all the variants of the target nucleic acid sequence. In many cases, the desired variant refers to a mutant allele and the undesired variant refers to a wild-type allele.

The term "wild-type" as used herein refers to a gene or allele which has the characteristics of that gene or allele when isolated from a naturally occurring source. A wild-type gene or a wild-type allele is that which is most frequently observed in a population and is arbitrarily designated as the "normal" or "wild-type" form of the gene or allele.

In contrast, the term "mutant" or "mutated" refers to a gene or allele which displays modifications in sequence when compared to the wild-type gene or allele. The term "mutation" refers to a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions (e.g. single nucleotide substitutions) and frame-shift mutations. The latter entail the insertion or deletion of one to several nucleotide pairs.

The term "allele" refers to two sequences which are different by only one or a few bases.

The term "mismatch" DNA or "heteroduplex" DNA refers to DNA which includes one or more mismatch base pairings. A mismatch base pairing refers to a specific pair of opposing bases, in the context of a DNA duplex, which cannot form one of the hydrogen-bonded base pairs, T with A or G with C. Heteroduplex DNA includes double-stranded DNA in which one or more bases in one strand does or do not complement the base or bases in the opposing strand, as well as double-stranded DNA in which one or more bases of either strand does or do not have an opposing base, due to an insertion or deletion in one strand as compared to the opposing strand. In contrast, homoduplex DNA refers to double-stranded DNA in which each strand is a complete complement of the other strand, and each base forms a hydrogen-bonded base pair with an opposing base.

The terms "molecular binding partners" and "specific binding partners" refer to pairs of molecules, typically pairs of biomolecules, that exhibit specific binding. Non-limiting examples are receptor and ligand, antibody and antigen, biotin and avidin, and biotin and streptavidin. Molecular binding partners can also be represented by binding that occurs between an "affinity label" and an "affinity matrix" as defined below.

An "affinity" label is a molecule that can specifically bind to its molecular binding partner. The binding can be through covalent or non-covalent (e.g., ionic, hydrogen, etc.) bonds. As used herein, an affinity label, such as biotin, can selectively bind to an affinity matrix, such as streptavidin-coated beads or particles.

An "affinity matrix" as used herein refers to a molecule that is attached to the surface of a solid support or solid matrix (e.g. magnetic latex particles, glass beads) that can specifically bind to its molecular binding partner. The binding can be through covalent or non-covalent bonds. As used herein, an affinity matrix, such as streptavidin-coated magnetic latex particles can selectively bind to an affinity label, such as biotin.

"PCR amplification" or simply "PCR" refers to the polymerase chain reaction that involves the use of a nucleic acid sequence as a template for producing a large number of complements to that sequence. The template may be hybridized to a primer having a sequence complementary to a portion of the template sequence and contacted with a suitable reaction mixture including dNTPs and a polymerase enzyme. The primer is elongated by the polymerase enzyme producing a nucleic acid complementary to the original template. For the amplification of both strands of a double stranded nucleic acid molecule, two primers are used, each of which may have a sequence which is complementary to a portion of one of the nucleic acid strands. The strands of the nucleic acid molecules are denatured, for example by heating, and the process is repeated, this time with the newly synthesized strands of the preceding step serving as templates in the subsequent steps. A PCR amplification protocol may involve a few to many cycles of denaturation, hybridization and elongation reactions to produce sufficient amounts of the target nucleic acid.

The term "allele-specific primer" or "AS primer" refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient, inefficient or undetectable.

The term "common primer" refers to the second primer in the pair of primers that includes an allele-specific primer. The common primer is not allele-specific, i.e. does not discriminate between the variants of the target sequence between which the allele-specific primer discriminates.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e. there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FF-PET) and nucleic acids isolated therefrom.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to the modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

As used herein, the term "target sequence", "target nucleic acid" or "target" refers to a portion of the nucleic acid sequence which is to be either amplified, detected or both.

The terms "hybridized" and "hybridization" refer to the base-pairing interaction of between two nucleic acids which results in formation of a duplex. It is not a requirement that two nucleic acids have 100% complementarity over their full length to achieve hybridization.

The terms "selective hybridization" and "specific hybridization" refer to the hybridization of a nucleic acid predominantly (50% or more of the hybridizing molecule) or nearly exclusively (90% or more of the hybridizing molecule) to a particular nucleic acid present in a complex mixture where other nucleic acids are also present. For example, under typical PCR conditions, primers specifically hybridize to the target nucleic acids to the exclusion of non-target nucleic acids also present in the solution. The specifically hybridized primers drive amplification of the target nucleic acid to produce an amplification product of the target nucleic acid that is at least the most predominant amplification product and is preferably the nearly exclusive (e.g., representing 90% or more of all amplification products in the sample) amplification product. Preferably, the non-specific amplification product is present in such small amounts that it is either non-detectable or is detected in such small amounts as to be easily distinguishable from the specific amplification product. Similarly, probes specifically hybridize to the target nucleic acids to the exclusion of non-target nucleic acids also present in the reaction mixture. The specifically hybridized probes allow specific detection of the target nucleic acid to generate a detectable signal that is at least the most predominant signal and is preferably the nearly exclusive (e.g., representing 90% or more of all amplification products in the sample) signal.

A key concern that faces clinical and diagnostic applications is the ability to detect clinically significant low-level mutations and minority alleles. The ability to detect mutations is important in many disease areas, but especially for early cancer detection from tissue biopsies and bodily fluids such as plasma or serum. Other areas where detecting rare mutations or alleles are significant include: disease staging and molecular profiling for prognosis or tailoring therapy to individual patients, and monitoring of therapy outcome and remission/relapse of the disease. Efficient detection of cancer-relevant mutations depends on the selectivity of the techniques and methods employed. Detection and identification of oncogene and tumor-suppressor gene mutations would require analysis of various types of samples, including pre-cancerous or cancerous tissue, sputum, urine, stool, and circulating extracellular DNA in blood. The sample is typically composed of both wild-type and mutant DNA, and the quantity of wild-type DNA often exceeds that of mutant DNA by $10^1$ to $10^8$ or $10^9$-fold, which makes detection and identification of these low-abundance mutations extremely difficult.

A number of methods have been employed to detect mutations. In one set of methods, polymerase chain reaction (PCR) is a component of the detection system. PCR is capable of specifically amplifying a target nucleic acid sequence (e.g. a mutant DNA) present amidst a much larger number of other sequences (e.g. wild-type DNA). Allele-specific PCR (AS-PCR) is a method capable of distinguishing between sequences that differ by as little as a single nucleotide. The sensitivity and specificity of PCR and AS-PCR is such that the target variant of the nucleic acid (e.g. mutant) can be selectively amplified even in the presence of much larger amounts of non-target variants (e.g. wild-type). For many AS-PCR assays, mutant DNA can be detected in an excess of wild-type DNA having a population 100 to 1,000 times greater than that of the mutant DNA. However, this level of sensitivity is insufficient for accurately detecting and identifying the extremely low concentration mutations present at ratios of $10^{-3}$ to $10^{-6}$ mutant to wild-type DNA. Therefore, the use of enrichment methods is often beneficial or necessary to increase the mutant concentration to a level such that accurate and precise detection can be attained.

In U.S. Pat. No. 6,031,098 (incorporated by reference herein), Barton et al. describe the synthesis and function of two families of mismatch-specific rhodium-based intercalators based on a pair of bulky intercalating ligands, 5,6-chrysenequinone diimine (chrysi) and 3,4-benzo[a]phenazine quinone diimine (phzi). The structures of these molecules are shown in FIG. 1. In both compounds, the sterically expansive ligand is too large to intercalate easily into the base stack of regular B-form DNA. However, the compounds are able to bind with high affinities to the thermodynamically destabilized mismatched sites. Binding affinities are in the order of $10^6 M^{-1}$ for $Rh(bpy)_2(chrysi)^{3+}$ and $10^8 M^{-1}$ for $Rh(bpy)_2(phzi)^{3+}$. Affinities correlate with the destabilization associated with a mismatch. The correlation between affinity and mismatch stabilization can be understood on the basis of the ease of extruding the mismatched bases when the metal complex is inserted into the base pair stack. The most destabilized sites are most easily bound by the metal complexes. In all, the compounds bind more than 80% of mismatch sites in all possible sequence contexts. These rhodium-based intercalators exhibit 1,000-fold or higher selectivity for mismatched DNA sites over Watson-Crick base-paired DNA sites. In addition to binding mismatches tightly and selectively, the complexes promote direct strand scission at the mismatch site upon photoactivation. A single mismatch within a 2 kb plasmid was shown to be capable of being bound and cleaved by these intercalator molecules.

The present invention utilizes the mismatch-binding properties of the rhodium-based intercalators and describes the synthesis of novel modified versions of the higher binding affinity compound, $Rh(bpy)_2(phzi)^{3+}$, that would allow its immobilization to a solid support. One example of such a modified rhodium chelator compound is shown on FIG. 2. By generating conditions whereby the low abundance mutant DNA are present as a heteroduplex that contains a single-base mismatch, the mutant DNA can be captured using the immobilized (phzi) intercalator and be separated from the excess amounts of wild-type DNA that do not contain a mismatch and cannot bind to the (phzi) intercalator. The enriched mutant DNA population can then be subject to amplification reactions (e.g. allele-specific PCR) for detection.

The following examples and figures are provided to aid the understanding of the present invention, the true scope of which is set forth in the appended claims. It is understood that modifications can be made in the procedures set forth without departing from the spirit of the invention.

EXAMPLES

Example 1

Synthesis of Methyl 5,6-dihydro-5,6-dioxobenzo[a]phenazine-9-carboxylate 2,3-dichloronapthalene-1,4-dione (4.5 g, 20 mmol), methyl 3,4-diaminobenzoate (3.32 g, 20 mmol), and 150 mL of pyridine were added to a 250 mL round-bottom flask and placed in a reflux condenser for one hour. The solution appeared to be dark reddish-brown, but did not form any sign of precipitate. The solution was left overnight to see if any precipitate will form in room temperature.

After allowing the reaction to cool overnight, precipitate was formed and filtered in a pre-weighed sintered glass funnel to yield a red-brown solid. The intermediate was rinsed with pyridine and dried overnight in a vacuum desiccator. The funnel was weighed again the next morning, and revealed that 5.7-g of the intermediate had been isolated. This entire amount was then in the oxidation step described below.

In the oxidation step, the intermediate was placed in a 250 ml round-bottom flask and 50 mL acetic acid, 3.0 mL deionized water, and 5 mL concentrated nitric acid were added carefully in that order, with vigorous magnetic stirring. The reaction mixture was then placed in a boiling bath and refluxed. A bright yellow precipitate began to form upon heating. Due to the heavy precipitate, the stir bar became immobilized. In order to alleviate this, a further 10-mL aliquot of glacial acetic acid was added. The reaction mixture was refluxed for one hour and then cooled to room temperature and filtered, yielding a golden yellow powdery solid. This product was also rinsed with 20 mL of each ethanol and diethyl ether and left to dry overnight.

Example 2

Synthesis: $[Rh(bpy)_2Cl_2]Cl$ $[Rh(bpy)_2Cl_2]Cl$ was prepared according to Zeglis, B. M. & Barton, J. K. Nat. Protoc. 2007, 2, 122-134. Briefly, RhCl3 (0.64 g, 2.8 mmol) and hydrazine monohydrochloride (50 mg, 7.35 mmol) were dissolved in 12.5 ml deionized water in a 50 ml round-bottom flask. A separately prepared solution made by dissolving 0.85 g (5.6 mmol) 2,2'-bipyridyl in 20-mL ethanol, and was also added to the same 50 ml round-bottom flask. The dissolved oxygen was removed by repeated applications of vacuum followed by back-filling with argon gas. This was followed by refluxing the reaction mixture until all the materials had dissolved. After refluxing for twenty minutes, the reaction became a bright orange solution and was filtered with a sintered glass filter funnel. It is important to filter the solution while it is hot to isolate only the product that was in solution and to reject any insoluble impurities. The filtrate was then stored overnight in 4° C. to promote crystallization.

The chilled filtrate was filtered, yielding a yellow crystalline solid. The mass of [Rh(bpy)2Cl2]Cl obtained was 780 mg and was stored at ambient temperature in a desiccated chamber.

Example 3

Synthesis: $[Rh(bpy)_2(OTf)_2]OTf$

[Rh(bpy)2Cl2]Cl (500 mg, 1.0 mmol), was placed in a 3-neck round-bottom flask with a 14/20 joint. Two rubber septums were placed on left and right neck ends of the flask and the adapter was placed at the center to allow hydrochloric acid to purge out. The flask was deoxygenated by evacuating any air contained followed by filling with argon gas. Triflic acid was then added carefully and quickly dissolved the [Rh(bpy)2Cl2]Cl to a yellow clear solution. Because the literature called for the reaction solution to stir for 16 hours, it was left overnight.

An acetone/dry ice bath was prepared for the next step where 300 ml diethyl ether was poured into a 1000 ml round-bottom flask, fitted with a drying tube, and cooled in the dry ice bath. The reaction mixture solution was poured into an addition tube and added to the cold diethyl ether solution dropwise. The reaction mixture appeared cloudy as a pale yellow solid precipitated at the bottom of the flask. The precipitated product was filtered through a weighed medium sintered glass funnel and was immediately placed in a vacuumed desiccator since it was found to be very sensitive to moisture. All of the material, whose yield was 750 mg, was used for the following step.

Example 4

Synthesis of $[Rh(bpy)_2(NH_3)_2](OTf)_3$

All of the [Rh(bpy)2(OTf)2]OTf, that was obtained in the previous reaction was placed in a 250 ml round-bottom flask. 30 ml of ammonium hydroxide was then added to the flask and stirred. The mixture was then refluxed and boiled for about 15 minutes until all of the components came into a pale yellow solution. Excess ammonium hydroxide was then removed by rotary evaporation, yielding a yellow-white solid. This product (final yield 720 mg) was dried overnight in a vacuum desiccator.

Example 5

Synthesis of [Rh(bpy)$_2$(phzi-CO2H)](Cl)$_3$

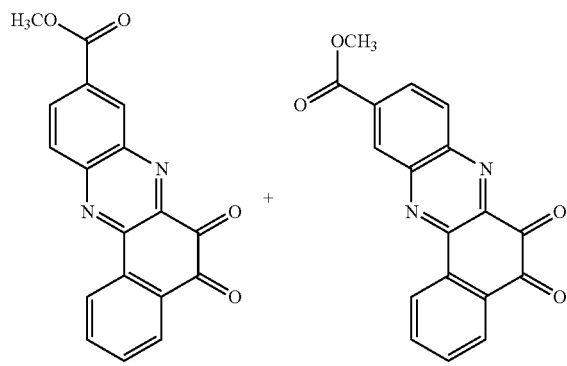

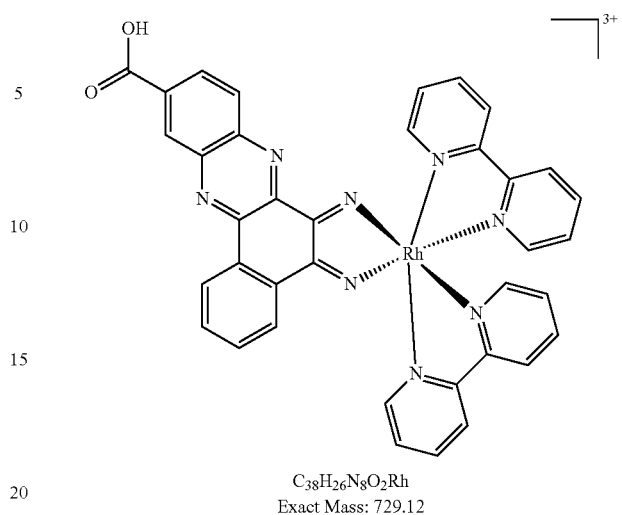

C$_{38}$H$_{26}$N$_8$O$_2$Rh
Exact Mass: 729.12

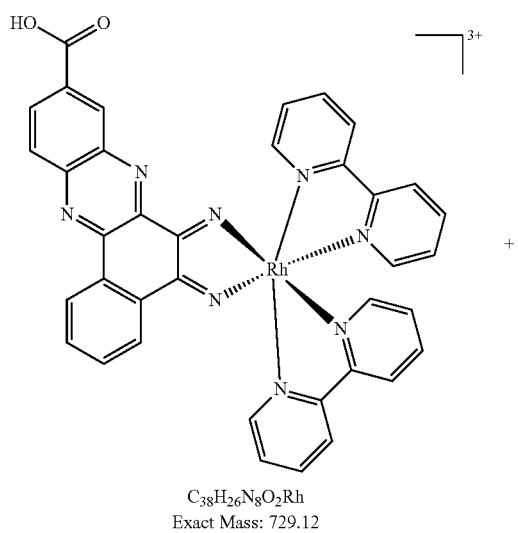

C$_{38}$H$_{26}$N$_8$O$_2$Rh
Exact Mass: 729.12

Quinone Ligand

A mixture of methyl 5,6-dihydro-5,6-dioxobenzo[a]phenazine-9-carboxylate methyl 5,6-dihydro-5,6-dioxobenzo[a]phenazine-10-carboxylate 500 mg of [Rh(bpy)2(NH3)2](OTf)3 (0.5 mmol) and 198.75 mg (0.625 mmoles) of the quinone ligand described above were dissolved in 250 mL acetonitrile at ambient temperature. Shortly afterwards, 10 mL of 0.4M sodium hydroxide was added to the reaction and was stirred for 3 hours in a closed vessel. Color changes were observed, signaling that a reaction has occurred. An LC-MS analysis of the reaction mixture revealed that during the alkaline conjugation conditions, the desired compound was obtained by in situ hydrolysis of the methyl ester intermediate. The reaction was then neutralized to pH 7 by adding incremental amounts of 0.4M hydrochloric acid, until a neutral pH was achieved. The acetonitrile contained in the reaction was removed by rotary evaporation at ambient temperature.

The resulting residue coated the flask and had a brown and yellow appearance, which was then dissolved in a small amount of deionized water (~25 mL). This solution was then stored in 4° C. overnight. The crude product was purified by reverse phase HPLC, using a semi-preparative column under the following conditions.

Column:

Waters Symmetry Shield RP8, 5 um, 7.8×300 mm, P/N WAT248000, L/N M90845D01

Buffers:

A 100 mM TEAA

B Acetonitrile

Flow Rate 6 mL/min

The column was equilibrated in 100% A buffer, and the entire sample amount (53-mL) was injected through the pump using 6 mL/min flow rate. After further washing with 100% A for 5 minutes, the gradient was initiated and 30-second (3-mL) fractions were collected.

The fractions were analyzed by LC-MS, and the purest fractions were pooled and lyophilized. LC-MS analysis showed the expected parent ion peak at M/e of 715 for the desired product, and a UV spectrum very similar to the parent rhodium complex.
Example 6
Synthesis of [Rh(bpy)$_2$(phzi)(PEG$_3$-Biotin)](Cl)$_3$
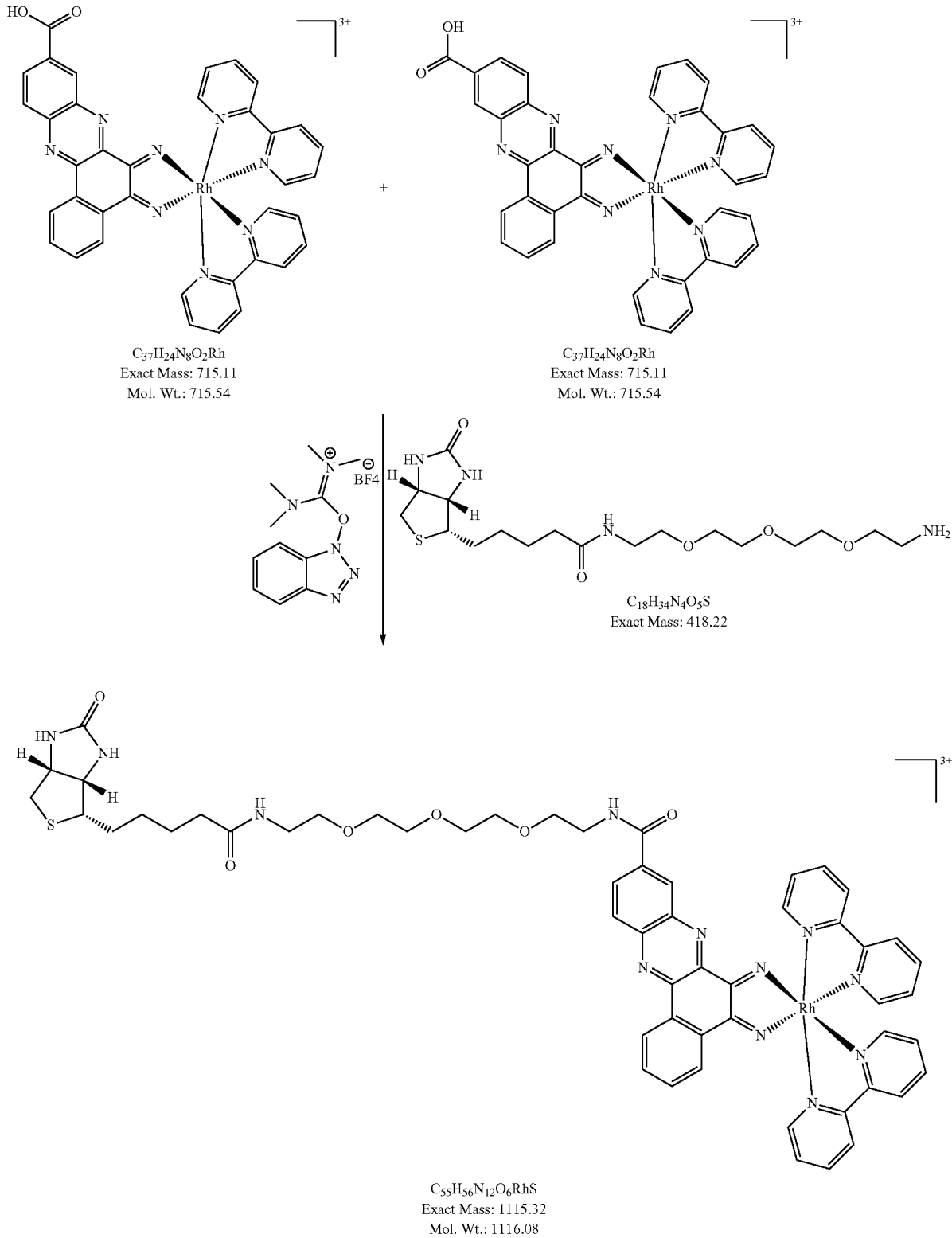

Figure 2:
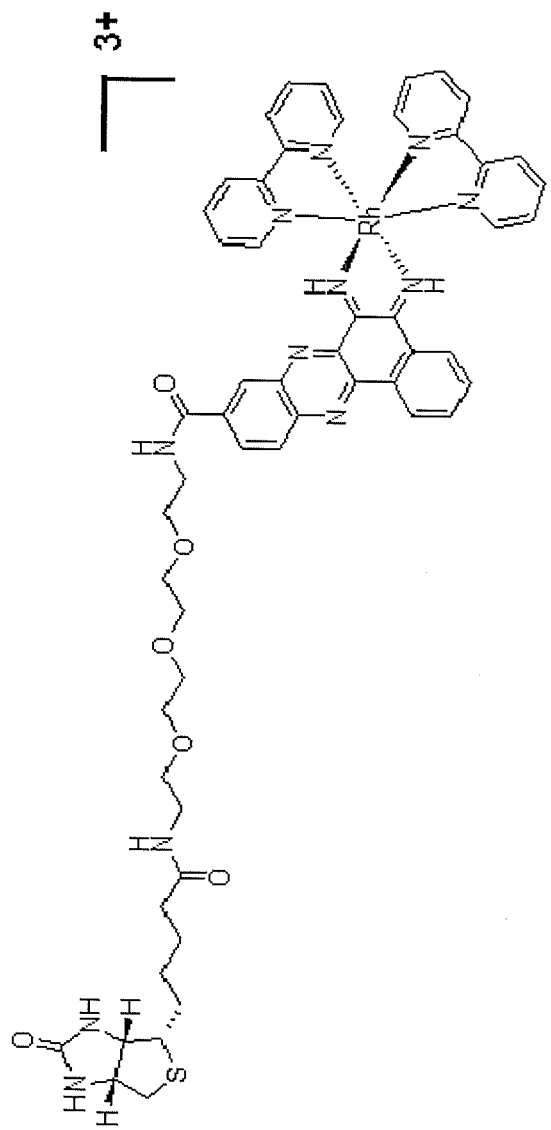
FIG. 2 shows the structure of the biotin-bound rhodium intercalator of the present invention, $Rh(bpy)_2(phzi)(PEG3-Biotin)^{3+}$

Rh(bpy)$_2$(phzi-COOH)Cl3 (160 mg, 195 µmoles) was dissolved in 20 mL DMF with vigorous magnetic stirring in a 250 mL round bottom flask. Separately, 100 mg (239 µmoles) of EZ-Link Amine-PEG3-Biotin (Thermo Scientific, product#21347) was dissolved in 40 mL acetonitrile. Note: A small amount of material remained undissolved. The EZ-Link Amine-PEG3-Biotin solution was added to the flask with stirring. Separately, a 0.5 M solution of TBTU [O-(Benzotriazol-1-yl)-N,N,N',N'-tetramethyluronium tetrafluoroborate] (Alfa Aesar, stock# L13470). was prepared in acetonitrile by dissolving 321 mg in 2-mL acetonitrile, and this was added to the reaction with stirring. The reaction was allowed to proceed at room temperature for 30 minutes, and the progress was monitored by withdrawing aliquots and analyzing by LC-MS. This analysis clearly showed that all the staring material had been consumed, and the major reaction product appeared to be the desired target molecule, [Rh(bpy)2(phzi)(PEG$_3$-Biotin)](Cl)$^3$ (FIG. 2). In addition, a closely eluting minor byproduct was also observed. The reaction was allowed to stir for 90 minutes. Some insoluble material was noted at this time, and the reaction mixture was filtered through a fluted filter paper. The filtrate was diluted to 500 mL with deionized water, and filtered again through a 0.45 micron filter. This material was stored in a refrigerator until needed for purification by reverse phase HPLC as described below.

LC-MS Analysis

The reaction above was analyzed by LC-MS using a C-8 reverse phase column and a linear gradient of 15-30% acetonitrile in 10 mM TEAA over 20 minutes.

Purification

A preparative reverse phase HPLC based method was developed as described below.

Column:

Waters Symmetry Shield RP8, 5 um, 7.8×300 mm, P/N WAT248000, L/N M90845D01

Buffers:

A 100 mM TEAA

B Acetonitrile

Flow Rate 3 mL/min

The column was equilibrated in 100% A buffer, and one-fifth (100-mL) of the crude product was injected through the pump using 4 mL/min flow rate. After further washing with 100% A for 5 minutes, the gradient was initiated and 60-second (3-mL) fractions were collected. The fractions were analyzed by LC-MS, and the purest fractions were pooled and lyophilized.

Example 7

Photocleavage of Mismatched DNA Using Rhodium Chelators

An assay was designated for testing the ability of the rhodium chelators to intercalate and promote strand scission upon photoactivation only with a DNA duplex that contains a mismatch site. Oligonucleotides attached with fluorescent dyes that span the T790M point mutation of the human Epidermal Growth Factor Receptor (EGFR) gene were synthesized with the following features. The oligonucleotide for the sense strand of the wild-type gene having a "C" allele at amino acid position 790 was attached with the FAM fluorophore (WT-S-FAM). The complementary oligonucleotide for the anti-sense strand of the wild-type gene (with a "G" residue) was attached with the JA270 fluorophore (WT-AS-JA270). The oligonucleotide for the sense strand of the T790M mutant gene having a "T" allele was attached with the HEX fluorophore (M-S-HEX). The complementary oligonucleotide for the anti-sense strand of the T790M mutant gene (with an "A" residue) was attached with the Cy5.5 fluorophore (M-AS-Cy5.5). Duplexes generated between the wild-type oligonucleotides and between the mutant oligonucleotides would be perfectly matched, whereas duplexes generated between one wild-type oligonucleotide and one mutant oligonucleotide would carry a mismatch at the site of the point mutation. For example, a duplex between the WT-S-FAM oligonucleotide and the M-AS-Cy5.5 oligonucleotide would contain a C:A mismatch which would be recognized by the rhodium chelator and be cleaved upon photoactivation.

Figure 3:
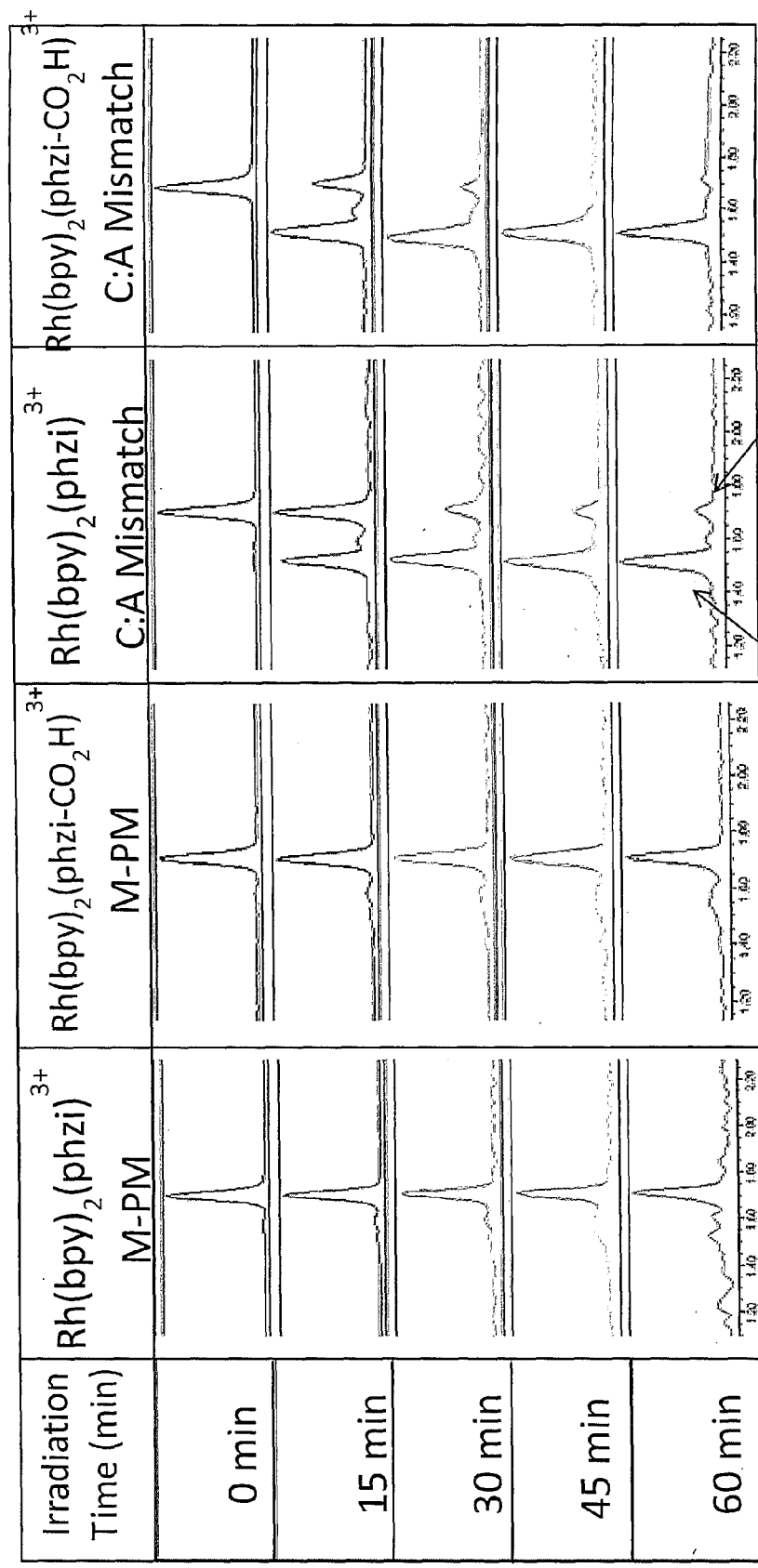
FIG. 3 shows an UPLC analysis of the cleavage efficiencies of $Rh(bpy)_2(phzi)^{3+}$ and $Rh(bpy)_2(phzi-CO_2H)^{3+}$ against the perfectly matched mutant duplex (M-PM) and the C:A mismatch duplex for the T790M mutation site in the human EGFR gene.

An experiment was performed in which 10 µM of either the parent rhodium chelator, Rh(bpy)$_2$(phzi)$^{3+}$ (FIG. 1) or the carboxyl intermediate rhodium chelator synthesized according to the protocol in Example 5, Rh(bpy)$_2$(phzi-CO2H)$^{3+}$, was incubated with 2 µM of an oligonucleotide pair consisting of either M-S-HEX and M-AS-Cy5.5 to generate a perfectly matched mutant duplex, or WT-S-FAM and M-AS-Cy5.5 to generate a C:A mismatch duplex. Following incubation, the solutions were irradiated at 365 nm wavelength using the UV Stratalinker™ 1800 (Stratagene) for an amount of time ranging from 0 minutes to 60 minutes and were analyzed using a Waters UPLC column and fluorescence detector for the presence or absence of cleavage. The results of the experiment are shown on FIG. 3. Both rhodium chelators show no cleavage occurring in the perfectly matched mutant duplex (M-PM columns). In contrast, efficient cleavage was observed in the C:A mismatch duplex with the disappearance of the intact oligonucleotide peak and the appearance of the cleaved oligonucleotide peak following UV irradiation. Similar results were observed when the chelators were incubated with the wild-type perfectly matched oligonucleotide duplex, although the carboxyl intermediate rhodium chelator exhibited a slight amount of non-specific cleavage (data not shown).

Example 8

Comparison of the Rhodium Chelators

Figure 4:
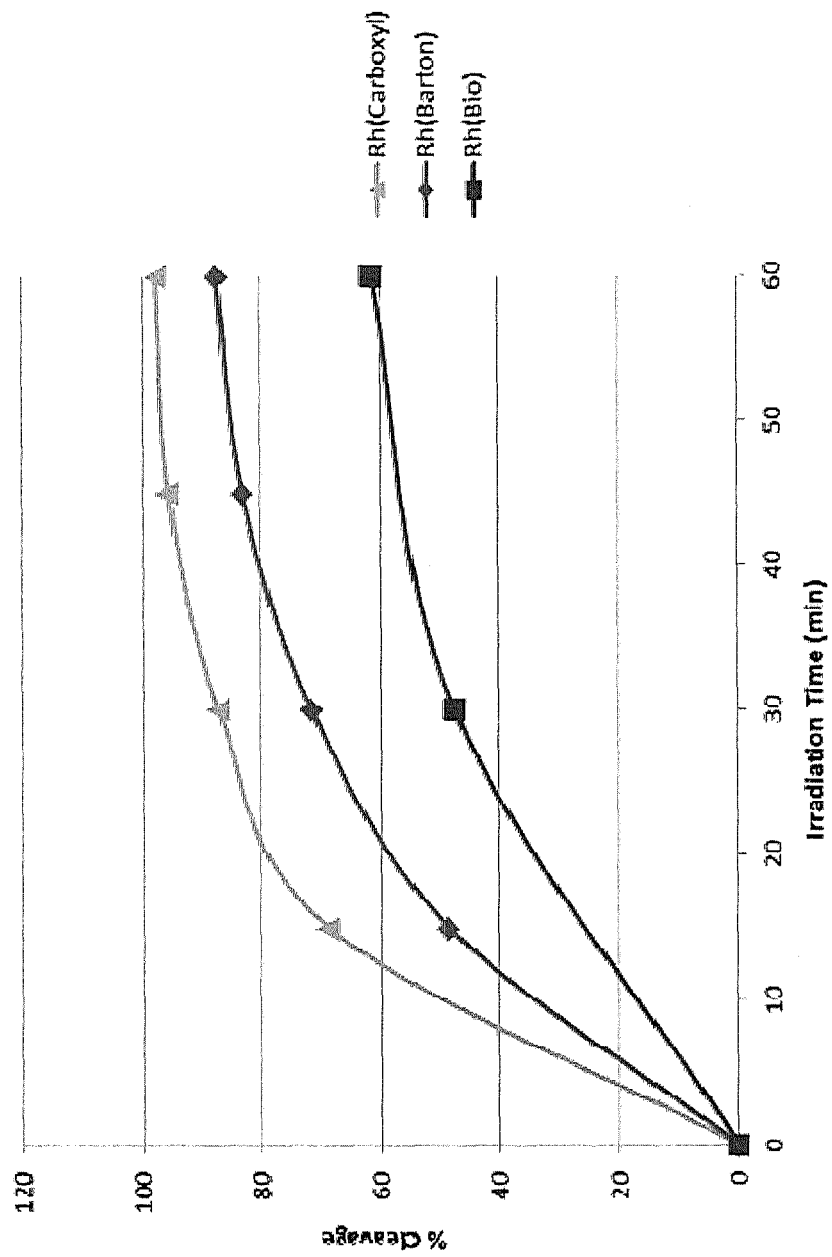
FIG. 4 is a graphical representation of the cleavage efficiencies of $Rh(bpy)_2(phzi-CO_2H)^{3+}$ (Rh(Carboxyl), $Rh(bpy)_2(phzi)^{3+}$ (Rh(Barton)), and $Rh(bpy)_2(phzi)(PEG3-Biotin)^{3+}$ (Rh(bio)) as a function of UV irradiation time.

An experiment using the same conditions as the one described in Example 7 was done to compare the performances of the parent rhodium chelator, Rh(bpy)$_2$(phzi)$^{3+}$, the carboxyl intermediate chelator, Rh(bpy)$_2$(phzi-CO2H)$^{3+}$, and the biotin-bound rhodium chelator, Rh(bpy)$_2$(phzi)(PEG$_3$-Biotin)$^{3+}$, in cleaving the oligonucleotide duplex that contained the C:A mismatch. 2 µM of the C:A mismatch duplex was incubated with 10 µM of the rhodium chelators which was followed by 0, 15, 30, 45, and 60 minutes of photoactivation. The results of this experiment are shown on FIG. 4. The biotin-bound rhodium chelator displayed approximately 60% cleavage of the duplex after 60 minutes of UV irradiation, as compared to 90-98% cleavage displayed by other two rhodium chelators.

Figure 5:
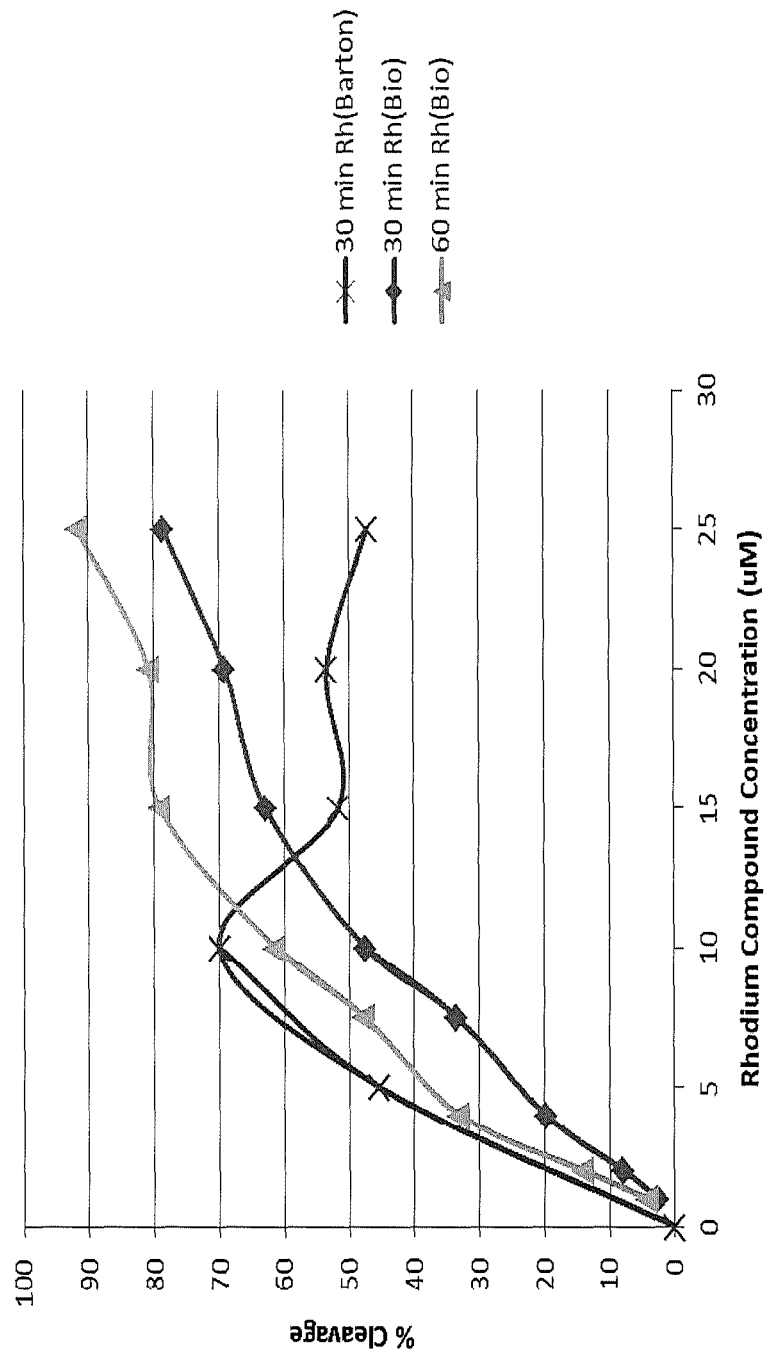
FIG. 5 is a graphical representation of the cleavage efficiencies of $Rh(bpy)_2(phzi)^{3+}$ (Rh(Barton)), after 30 minute UV irradiation and $Rh(bpy)_2(phzi)(PEG3-Biotin)^{3+}$ (Rh (bio)) after 30 minute or 60 minute UV irradiation as a function of the concentration of each rhodium chelator.

Next, the cleavage activity of the biotin-bound rhodium chelator using different concentrations of the chelator was investigated and compared to the cleavage activity of the parent rhodium chelator at the same concentration range. The results are shown on FIG. 5. At 5 µM and 10 µM concentrations, the parent rhodium chelator displayed greater cleavage efficiency than the biotin-bound rhodium chelator. However at concentrations above 15 µM, the parent chelator displayed inconsistent cleavage efficiency, whereas the biotin-bound rhodium chelator exhibited efficient cleavage at these higher concentrations with more than 90% cleavage observed at a concentration of 25 μM following 60 minutes of UV irradiation.

Example 9

Enrichment and Detection of Mutant DNA Using Rh(bpy)$_2$(phzi)(PEG$_3$-Biotin)$^{3+}$ A sample is provided from which a mixture of nucleic acids, for example, human genomic DNA, can be extracted. The sample can be from a tissue such as skin, organs, and tumors or from fluid such as blood, plasma, serum, urine, or from any composition containing or presumed to contain nucleic acid. From this mixture of nucleic acids, a target gene of interest, for example, the human EGFR gene, may contain a certain variation such as a point mutation that is present in low abundance amongst a large excess of the other variant of the gene, which would be the non-mutant or wild-type gene.

To enrich for the low-abundance mutant allele of the target gene, an excess of an oligonucleotide (oligo C) that is complementary to and perfectly matched with one of the strands (e.g. the sense strand or strand S) of the wild-type allele of the target gene is added to a solution containing the extracted genomic DNA. The solution is then heated at 90° C. or higher temperature to denature the double-stranded genomic DNA and then gradually cooled to a temperature to allow reannealing of the single DNA strands to occur. During the annealing step, some strand S: oligo C duplexes can form in which the wild-type DNA-strand S: oligo C hybrids will be perfectly matched, but the mutant DNA-strand S: oligo C duplexes will have a mismatch at the position of the point mutation.

The biotin-bound rhodium chelator, Rh(bpy)$_2$(phzi)(PEG3-Biotin)$^{3+}$, is then added to the solution and allowed to incubate such that the chelator can bind to the mutant DNA-strand S: oligo C duplexes at the position of the mismatch. Next, a solid matrix coated with streptavidin is added. Examples of such solid matrices would be streptavidin coated magnetic particles such as Streptavidin-coupled Dynabeads® from Invitrogen, Streptavidin MagneSphere® Paramagnetic Particles from Promega, and NanoLink™ and MagnaLink™ Streptavidin Magnetic Beads from Solulink. Following incubation (e.g. 40° C. for 1 hour), a magnet is used to separate the particles and wash away all the nucleic acid that is not bound to the particles, which includes the wild-type DNA and the excess of oligo C. The bound mutant DNA-strand S is then eluted from the magnetic particles using an appropriate elution buffer and can then serve as a template for use in an amplification reaction. Using the EGFR gene as an example, various mutant EGFR alleles can be amplified using the allele-specific primers and TaqMan® probes under the real-time PCR conditions disclosed in U.S. patent application Ser. No. 13/324,705, which is incorporated by reference herein.

In an alternate method to enrich for the low-abundance mutant allele of the target gene, the sample is heated at high temperature (e.g. 95° C.) sufficient for denaturation of the mixture of nucleic acids into single-stranded molecules. The temperature is then lowered to allow each single strand to reanneal with its complementary strand. All or almost all of the single strands that carry the mutant allele is annealed to a complementary strand that contains the wild-type allele to form mutant:wild-type mismatch duplexes. The biotin-bound rhodium chelator, Rh(bpy)$_2$(phzi)(PEG3-Biotin)$^{3+}$, is then added to the solution and allowed to incubate such that the chelator can bind specifically to the mismatch duplexes. The rest of the experiment is conducted as described above resulting in an enriched population of the mutant DNA which can be used in an amplification reaction for detection.

While the invention has been described in detail with reference to specific examples, it will be apparent to one skilled in the art that various modifications can be made within the scope of this invention. Thus the scope of the invention should not be limited by the examples described herein, but by the claims presented below.

The invention claimed is:

1. A method of enriching a variant of a target nucleic acid sequence in a mixture of nucleic acids from a sample, the target nucleic acid existing in the form of two variant sequences, wherein said variants differ at a single nucleotide position, the method comprising:
    providing the sample that includes the target nucleic acid sequence wherein the variant to be enriched is present in the sample in low abundance amongst a large excess of the other variant;
    providing an oligonucleotide that is complementary to one strand of the target nucleic acid sequence, wherein the oligonucleotide has a mismatch at the single nucleotide position with the variant to be enriched and is perfectly matched at the single nucleotide position with the other variant;
    providing conditions suitable for hybridization of the oligonucleotide to the target nucleic acid to generate duplex polynucleotides consisting of the oligonucleotide and one strand of either variant of the target nucleic acid sequence;
    contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch;
    subjecting the reaction mixture to an affinity matrix that recognizes and binds to the affinity label on the mismatch intercalating compound;
    washing the reaction mixture and separating the affinity matrix from all material that is not bound to the affinity matrix; and
    providing a buffer to elute nucleic acid from the affinity matrix, and collecting the eluted buffer which contains the enriched variant of the target nucleic acid sequence;
    wherein the mismatch intercalating compound with the affinity label is Rh(bpy)$_2$(phzi)(PEG3-Biotin)$^{3+}$.

2. The method of claim 1 wherein the variant to be enriched is a mutant allele and the other variant is a wild-type allele.

3. The method of claim 2 wherein the mutant allele is a mutant EGFR allele and the wild-type allele is a wild-type EGFR allele.

4. A method for detecting a mutant allele of a target nucleic acid sequence in a mixture of nucleic acids from a sample wherein the mutant allele differs from a wild-type allele at a single nucleotide position and is present in the sample in low abundance amongst a large excess of the wild-type allele, the method comprising:
    enriching the mutant allele in the sample wherein the enrichment is performed by providing an oligonucleotide that is complementary to one strand of the target nucleic acid sequence, wherein the oligonucleotide has a mismatch at the single nucleotide position with the mutant allele and is perfectly matched at the single nucleotide position with the wild-type allele;

providing conditions suitable for hybridization of the oligonucleotide to the target nucleic acid to generate duplex polynucleotides consisting of the oligonucleotide and one strand of either the mutant allele or the wild-type allele;

contacting the duplex polynucleotides with a mismatch intercalating compound that is attached with an affinity label to generate a reaction mixture, wherein the mismatch intercalating compound is capable of binding to the duplex polynucleotides that contain a mismatch and is not capable of binding to the duplex polynucleotides that do not contain a mismatch;

subjecting the reaction mixture to a affinity matrix that recognizes and binds to the affinity label on the mismatch intercalating compound;

washing the reaction mixture and separating the affinity matrix from all material that is not bound to the affinity matrix; and providing a buffer to elute nucleic acid from the affinity matrix, and collecting the eluted buffer which contains the enriched mutant allele;

amplifying the enriched mutant allele; and detecting the product of the enriched amplified mutant allele or the signal generated from the enriched amplified mutant allele;

wherein the mismatch intercalating compound with the affinity label is $Rh(bpy)_2(phzi)(PEG3\text{-}Biotin)^{3+}$.

5. The method of claim 4 wherein the mutant allele is a mutant EGFR allele and the wild-type allele is a wild-type EGFR allele.

6. The method of claim 4 wherein the amplifying step is performed with allele-specific primers.

7. A method of enriching a variant of a target nucleic acid sequence in a mixture of nucleic acids from a sample, the target nucleic acid existing in the form of two variant sequences, wherein said variants differ at a single nucleotide position, the method comprising:

providing the sample that includes the target nucleic acid sequence wherein the variant to be enriched is present in the sample in low abundance amongst a large excess of the other variant;

heating the sample such that the mixture of nucleic acid is denatured;

providing conditions suitable for the reannealing of the target nucleic acid, wherein duplex polynucleotides can be formed between one strand of one variant sequence and one strand of the other variant sequence to generate a mismatch at the single nucleotide position where the variants differ;

contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch;

subjecting the reaction mixture to an affinity matrix that recognizes and binds to the affinity label on the mismatch intercalating compound;

washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence;

wherein the mismatch intercalating compound with the affinity label is $Rh(bpy)_2(phzi)(PEG3\text{-}Biotin)^{3+}$.

8. The method of claim 7 wherein the variant to be enriched is a mutant allele and the other variant is a wild-type allele.

9. The method of claim 8 wherein the mutant allele is a mutant EGFR allele and the wild-type allele is a wild-type EGFR allele.

10. A method for detecting a mutant allele of a target nucleic acid sequence in a mixture of nucleic acids from a sample wherein the mutant allele differs from a wild-type allele at a single nucleotide position and is present in the sample in low abundance amongst a large excess of the wild-type allele, the method comprising:

enriching the mutant allele in the sample wherein the enrichment is performed by heating the sample such that the mixture of nucleic acid is denatured;

providing conditions suitable for the reannealing of the target nucleic acid, wherein duplex polynucleotides can be formed between one strand of the mutant allele and one strand of the wild-type allele to generate a mismatch at the single nucleotide position where the alleles differ;

contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch;

subjecting the reaction mixture to an affinity matrix that recognizes and binds to the affinity label on the mismatch intercalating compound;

washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence;

amplifying the enriched mutant allele; and detecting the product of the enriched amplified mutant allele or the signal generated from the enriched amplified mutant allele;

wherein the mismatch intercalating compound with the affinity label is $Rh(bpy)_2(phzi)(PEG3\text{-}Biotin)^{3+}$.

11. The method of claim 10 wherein the mutant allele is a mutant EGFR allele and the wild-type allele is a wild-type EGFR allele.

12. The method of claim 10 wherein the amplifying step is performed with allele-specific primers.

\* \* \* \* \*